(12) United States Patent
Kubacki

(10) Patent No.: US 12,396,739 B2
(45) Date of Patent: Aug. 26, 2025

(54) GUIDANCE TOOLS, SYSTEMS, AND METHODS

(71) Applicant: Wright Medical Technology, Inc., Memphis, TN (US)

(72) Inventor: Meghan Kubacki, Memphis, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 531 days.

(21) Appl. No.: 17/776,893

(22) PCT Filed: Dec. 16, 2020

(86) PCT No.: PCT/US2020/065189
§ 371 (c)(1),
(2) Date: May 13, 2022

(87) PCT Pub. No.: WO2021/146015
PCT Pub. Date: Jul. 22, 2021

(65) Prior Publication Data
US 2022/0401115 A1    Dec. 22, 2022

Related U.S. Application Data

(60) Provisional application No. 62/962,610, filed on Jan. 17, 2020.

(51) Int. Cl.
*A61B 17/17* (2006.01)
*A61B 17/16* (2006.01)
*A61B 17/00* (2006.01)

(52) U.S. Cl.
CPC ........ *A61B 17/1717* (2013.01); *A61B 17/164* (2013.01); *A61B 2017/00867* (2013.01)

(58) Field of Classification Search
CPC ............ A61B 5/6853; A61B 17/12022; A61B 17/12136; A61B 2017/22048; A61B 2017/22054; A61B 17/1631; A61B 17/164; A61B 17/1717; A61B 17/1796; A61B 17/320758; A61B 2017/3486; A61B 17/7208; A61B 17/8897; A61B 17/90
See application file for complete search history.

(56) References Cited

U.S. PATENT DOCUMENTS 3,314,420 A   4/1967   Smith et al.
3,605,123 A   9/1971   Hahn
(Continued)

FOREIGN PATENT DOCUMENTS

CN   1662186   8/2005
CN   101111197   1/2008
(Continued)

OTHER PUBLICATIONS

International Search Report and Written Opinion for PCT/US2020/065189 issued Apr. 20, 2021, 10 pages.
(Continued)

*Primary Examiner* — Larry E Waggle, Jr.
(74) *Attorney, Agent, or Firm* — DUANE MORRIS LLP

(57) ABSTRACT

A guidance tool includes a body having a length extending from a first end to a second end. The body includes a shape memory section along the length of the body. The shape memory section has a curved shape.

6 Claims, 4 Drawing Sheets

(56) References Cited

U.S. PATENT DOCUMENTS

| | | |
|---|---|---|
| 3,708,883 A | 1/1973 | Flander |
| 3,798,679 A | 3/1974 | Ewald |
| 3,808,606 A | 5/1974 | Tronzo |
| 3,843,975 A | 10/1974 | Tronzo |
| 3,855,638 A | 12/1974 | Pilliar |
| 3,938,198 A | 2/1976 | Kahn et al. |
| 3,987,499 A | 10/1976 | Scharbach et al. |
| 4,052,753 A | 10/1977 | Dedo |
| 4,055,862 A | 11/1977 | Farling |
| 4,085,466 A | 4/1978 | Goodfellow et al. |
| 4,098,626 A | 7/1978 | Graham et al. |
| 4,203,444 A | 5/1980 | Bonnell et al. |
| 4,213,816 A | 7/1980 | Morris |
| 4,340,978 A | 7/1982 | Buechel et al. |
| 4,368,040 A | 1/1983 | Weissman |
| 4,436,684 A | 3/1984 | White |
| 4,501,266 A | 2/1985 | McDaniel |
| 4,502,161 A | 3/1985 | Wall |
| 4,578,806 A | 3/1986 | Grass et al. |
| 4,586,496 A | 5/1986 | Keller |
| 4,594,380 A | 6/1986 | Chapin et al. |
| 4,601,290 A | 7/1986 | Effron et al. |
| 4,609,551 A | 9/1986 | Caplan et al. |
| 4,627,853 A | 12/1986 | Campbell et al. |
| 4,703,751 A | 11/1987 | Pohl |
| 4,704,686 A | 11/1987 | Aldinger |
| 4,715,860 A | 12/1987 | Amstutz et al. |
| 4,721,104 A | 1/1988 | Kaufman et al. |
| 4,759,350 A | 7/1988 | Dunn et al. |
| 4,769,040 A | 9/1988 | Wevers |
| 4,841,975 A | 6/1989 | Woolson |
| 4,846,835 A | 7/1989 | Grande |
| 4,865,607 A | 9/1989 | Witzel et al. |
| 4,880,429 A | 11/1989 | Stone |
| 4,936,862 A | 6/1990 | Walker et al. |
| 4,979,949 A | 12/1990 | Matsen, III et al. |
| 5,002,547 A | 3/1991 | Poggie |
| 5,041,138 A | 8/1991 | Vacanti et al. |
| 5,059,216 A | 10/1991 | Winters |
| 5,067,964 A | 11/1991 | Richmond et al. |
| 5,122,144 A | 6/1992 | Bert et al. |
| 5,129,908 A | 7/1992 | Petersen |
| 5,133,759 A | 7/1992 | Turner |
| 5,154,717 A | 10/1992 | Matsen, III et al. |
| 5,162,430 A | 11/1992 | Rhee et al. |
| 5,171,322 A | 12/1992 | Kenny |
| 5,197,985 A | 3/1993 | Caplan et al. |
| 5,206,023 A | 4/1993 | Hunziker |
| 5,226,914 A | 7/1993 | Caplan et al. |
| 5,234,433 A | 8/1993 | Bert et al. |
| 5,250,050 A | 10/1993 | Poggie et al. |
| 5,258,032 A | 11/1993 | Bertin |
| 5,270,300 A | 12/1993 | Hunziker |
| 5,288,797 A | 2/1994 | Khalil et al. |
| 5,303,148 A | 4/1994 | Mattson et al. |
| 5,306,311 A | 4/1994 | Stone et al. |
| 5,314,482 A | 5/1994 | Goodfellow et al. |
| 5,344,459 A | 9/1994 | Swartz |
| 5,360,446 A | 11/1994 | Kennedy |
| 5,365,996 A | 11/1994 | Crook |
| 5,368,858 A | 11/1994 | Hunziker |
| 5,370,692 A | 12/1994 | Fink et al. |
| 5,380,332 A | 1/1995 | Ferrante |
| 5,387,216 A | 2/1995 | Thornhill et al. |
| 5,454,816 A | 10/1995 | Ashby |
| 5,462,550 A | 10/1995 | Dietz et al. |
| 5,468,787 A | 11/1995 | Braden et al. |
| 5,474,559 A | 12/1995 | Bertin et al. |
| 5,478,739 A | 12/1995 | Slivka et al. |
| 5,486,180 A | 1/1996 | Dietz et al. |
| 5,501,687 A | 3/1996 | Willert et al. |
| 5,503,162 A | 4/1996 | Athanasiou et al. |
| 5,509,919 A * | 4/1996 | Young ............... A61B 17/1717 606/80 |
| 5,520,695 A | 5/1996 | Luckman |
| 5,523,843 A | 6/1996 | Yamane et al. |
| 5,540,696 A | 7/1996 | Booth, Jr. et al. |
| 5,542,947 A | 8/1996 | Treacy |
| 5,554,190 A | 9/1996 | Draenert |
| 5,556,432 A | 9/1996 | Kubein-Meesenburg et al. |
| 5,571,205 A | 11/1996 | James |
| 5,575,793 A | 11/1996 | Carls et al. |
| 5,578,037 A | 11/1996 | Sanders et al. |
| 5,593,450 A | 1/1997 | Scott et al. |
| 5,597,379 A | 1/1997 | Haines et al. |
| 5,601,563 A | 2/1997 | Burke et al. |
| 5,613,970 A | 3/1997 | Houston et al. |
| 5,616,146 A | 4/1997 | Murray |
| 5,630,820 A | 5/1997 | Todd |
| 5,632,745 A | 5/1997 | Schwartz |
| 5,649,929 A | 7/1997 | Callaway |
| 5,658,290 A | 8/1997 | Techeira |
| 5,671,741 A | 9/1997 | Lang et al. |
| 5,682,886 A | 11/1997 | Delp et al. |
| 5,683,466 A | 11/1997 | Vitale |
| 5,684,562 A | 11/1997 | Fujieda |
| 5,688,282 A | 11/1997 | Baron et al. |
| 5,728,162 A | 3/1998 | Eckhoff |
| 5,735,277 A | 4/1998 | Schuster |
| 5,749,874 A | 5/1998 | Schwartz |
| 5,749,876 A | 5/1998 | Duvillier et al. |
| 5,765,561 A | 6/1998 | Chen et al. |
| 5,768,134 A | 6/1998 | Swaelens et al. |
| 5,769,899 A | 6/1998 | Schwartz et al. |
| 5,782,842 A | 7/1998 | Kloess et al. |
| 5,786,217 A | 7/1998 | Tuba et al. |
| 5,798,924 A | 8/1998 | Eufinger et al. |
| 5,800,438 A | 9/1998 | Tuke et al. |
| 5,824,083 A | 10/1998 | Draenert |
| 5,827,289 A | 10/1998 | Reiley et al. |
| 5,830,216 A | 11/1998 | Insall et al. |
| 5,835,619 A | 11/1998 | Morimoto et al. |
| 5,842,477 A | 12/1998 | Naughton et al. |
| 5,847,804 A | 12/1998 | Sarver et al. |
| 5,853,746 A | 12/1998 | Hunziker |
| 5,860,981 A | 1/1999 | Bertin et al. |
| 5,871,018 A | 2/1999 | Delp et al. |
| 5,871,542 A | 2/1999 | Goodfellow et al. |
| 5,871,546 A | 2/1999 | Colleran et al. |
| 5,879,390 A | 3/1999 | Kubein-Meesenburg et al. |
| 5,880,976 A | 3/1999 | DiGioia, III et al. |
| 5,885,296 A | 3/1999 | Masini |
| 5,885,297 A | 3/1999 | Matsen, III |
| 5,885,298 A | 3/1999 | Herrington et al. |
| 5,897,559 A | 4/1999 | Masini |
| 5,899,859 A | 5/1999 | Votruba et al. |
| 5,900,245 A | 5/1999 | Sawhney et al. |
| 5,906,934 A | 5/1999 | Grande et al. |
| 5,910,143 A | 6/1999 | Cripe et al. |
| 5,911,723 A | 6/1999 | Ashby et al. |
| 5,916,220 A | 6/1999 | Masini |
| 5,939,323 A | 8/1999 | Valentini et al. |
| 5,951,475 A | 9/1999 | Gueziec et al. |
| 5,961,523 A | 10/1999 | Masini |
| 5,968,051 A | 10/1999 | Luckman et al. |
| 5,972,385 A | 10/1999 | Liu et al. |
| 5,995,738 A | 11/1999 | DiGioia, III et al. |
| 6,001,895 A | 12/1999 | Harvey et al. |
| 6,002,859 A | 12/1999 | DiGioia, III et al. |
| 6,006,126 A | 12/1999 | Cosman |
| 6,007,537 A | 12/1999 | Burkinshaw et al. |
| 6,010,509 A | 1/2000 | Delgado et al. |
| 6,013,081 A | 1/2000 | Burkinshaw et al. |
| 6,013,103 A | 1/2000 | Kaufman et al. |
| 6,046,379 A | 4/2000 | Stone et al. |
| 6,056,754 A | 5/2000 | Haines et al. |
| 6,056,756 A | 5/2000 | Eng et al. |
| 6,057,927 A | 5/2000 | Levesque et al. |
| 6,077,270 A | 6/2000 | Katz |
| 6,082,364 A | 7/2000 | Balian et al. |
| 6,090,144 A | 7/2000 | Letot et al. |
| 6,093,204 A | 7/2000 | Stone |
| 6,096,043 A | 8/2000 | Techeira et al. |
| 6,102,916 A | 8/2000 | Masini |

(56) References Cited

U.S. PATENT DOCUMENTS

| | | |
|---|---|---|
| 6,106,529 A | 8/2000 | Techiera |
| 6,110,209 A | 8/2000 | Stone |
| 6,120,541 A | 9/2000 | Johnson |
| 6,126,690 A | 10/2000 | Ateshian et al. |
| 6,139,578 A | 10/2000 | Lee et al. |
| 6,156,069 A | 12/2000 | Amstutz |
| 6,161,080 A | 12/2000 | Aouni-Ateshian et al. |
| 6,187,010 B1 | 2/2001 | Masini |
| 6,200,606 B1 | 3/2001 | Peterson et al. |
| 6,203,546 B1 | 3/2001 | MacMahon |
| 6,203,576 B1 | 3/2001 | Afriat et al. |
| 6,205,411 B1 | 3/2001 | DiGioia, III et al. |
| 6,206,927 B1 | 3/2001 | Fell et al. |
| 6,214,369 B1 | 4/2001 | Grande et al. |
| 6,217,894 B1 | 4/2001 | Sawhney et al. |
| 6,219,571 B1 | 4/2001 | Hargreaves et al. |
| 6,224,632 B1 | 5/2001 | Pappas et al. |
| 6,235,060 B1 | 5/2001 | Kubein-Meesenburg et al. |
| 6,251,143 B1 | 6/2001 | Schwartz et al. |
| 6,254,639 B1 | 7/2001 | Peckitt |
| 6,277,151 B1 | 8/2001 | Lee et al. |
| 6,281,195 B1 | 8/2001 | Rueger et al. |
| 6,283,980 B1 | 9/2001 | Vibe-Hansen et al. |
| 6,296,646 B1 | 10/2001 | Williamson |
| 6,299,905 B1 | 10/2001 | Peterson et al. |
| 6,322,588 B1 | 11/2001 | Ogle et al. |
| 6,327,491 B1 | 12/2001 | Franklin et al. |
| 6,328,765 B1 | 12/2001 | Hardwick et al. |
| 6,344,043 B1 | 2/2002 | Pappas |
| 6,344,059 B1 | 2/2002 | Krakovits et al. |
| 6,352,558 B1 | 3/2002 | Spector |
| 6,358,253 B1 | 3/2002 | Torrie et al. |
| 6,365,405 B1 | 4/2002 | Salzmann et al. |
| 6,371,958 B1 | 4/2002 | Overaker |
| 6,373,250 B1 | 4/2002 | Tsoref et al. |
| 6,375,658 B1 | 4/2002 | Hangody et al. |
| 6,379,367 B1 | 4/2002 | Vibe-Hansen et al. |
| 6,382,028 B1 | 5/2002 | Wooh et al. |
| 6,383,228 B1 | 5/2002 | Schmotzer |
| 6,387,131 B1 | 5/2002 | Miehlke et al. |
| 6,409,767 B1 | 6/2002 | Perice et al. |
| 6,429,013 B1 | 8/2002 | Halvorsen et al. |
| 6,443,988 B2 | 9/2002 | Felt et al. |
| 6,443,991 B1 | 9/2002 | Running |
| 6,444,222 B1 | 9/2002 | Asculai et al. |
| 6,459,927 B1 | 10/2002 | Franklin et al. |
| 6,459,948 B1 | 10/2002 | Ateshian et al. |
| 6,468,314 B2 | 10/2002 | Schwartz et al. |
| 6,478,799 B1 | 11/2002 | Williamson |
| 6,479,996 B1 | 11/2002 | Hoogeveen et al. |
| 6,510,334 B1 | 1/2003 | Schuster et al. |
| 6,520,964 B2 | 2/2003 | Tallarida et al. |
| 6,558,421 B1 | 5/2003 | Fell et al. |
| 6,560,476 B1 | 5/2003 | Pelletier et al. |
| 6,575,980 B1 | 6/2003 | Robie et al. |
| 6,620,168 B1 | 9/2003 | Lombardo et al. |
| 6,626,945 B2 | 9/2003 | Simon et al. |
| 6,626,948 B2 | 9/2003 | Storer et al. |
| 6,632,225 B2 | 10/2003 | Sanford et al. |
| 6,632,235 B2 | 10/2003 | Weikel et al. |
| 6,652,587 B2 | 11/2003 | Felt et al. |
| 6,673,077 B1 | 1/2004 | Katz |
| 6,679,917 B2 | 1/2004 | Ek |
| 6,712,856 B1 | 3/2004 | Carignan et al. |
| 6,738,657 B1 | 5/2004 | Franklin et al. |
| 6,905,514 B2 | 6/2005 | Carignan et al. |
| 6,916,341 B2 | 7/2005 | Rolston |
| 6,928,742 B2 | 8/2005 | Broers et al. |
| 6,932,842 B1 | 8/2005 | Litschko et al. |
| 6,942,667 B1 | 9/2005 | Song |
| 6,944,518 B2 | 9/2005 | Roose |
| 6,969,393 B2 | 11/2005 | Pinczewski et al. |
| 6,980,849 B2 | 12/2005 | Sasso |
| 6,988,015 B1 | 1/2006 | Schopf et al. |
| 6,993,374 B2 | 1/2006 | Sasso |
| 7,008,430 B2 | 3/2006 | Dong et al. |
| 7,058,439 B2 | 6/2006 | Eaton et al. |
| 7,060,074 B2 | 6/2006 | Rosa et al. |
| 7,104,997 B2 | 9/2006 | Lionberger et al. |
| 7,115,131 B2 | 10/2006 | Engh et al. |
| 7,117,027 B2 | 10/2006 | Zheng et al. |
| 7,141,053 B2 | 11/2006 | Rosa et al. |
| 7,184,814 B2 | 2/2007 | Lang et al. |
| 7,201,762 B2 | 4/2007 | Green, Jr. et al. |
| 7,217,276 B2 | 5/2007 | Henderson et al. |
| 7,239,908 B1 | 7/2007 | Alexander et al. |
| 7,245,697 B2 | 7/2007 | Lang |
| 7,250,055 B1 | 7/2007 | Vanderwalle |
| 7,282,054 B2 | 10/2007 | Steffensmeier et al. |
| 7,292,674 B2 | 11/2007 | Lang |
| 7,347,690 B2 | 3/2008 | Jordan et al. |
| 7,364,581 B2 | 4/2008 | Michalowicz |
| 7,377,924 B2 | 5/2008 | Raistrick et al. |
| 7,379,529 B2 | 5/2008 | Lang |
| 7,467,892 B2 | 12/2008 | Lang et al. |
| 7,468,075 B2 | 12/2008 | Lang et al. |
| 7,534,246 B2 | 5/2009 | Reiley et al. |
| 7,534,263 B2 | 5/2009 | Burdulis, Jr. et al. |
| 7,618,451 B2 | 11/2009 | Berez et al. |
| 7,747,305 B2 | 6/2010 | Dean et al. |
| 7,806,896 B1 | 10/2010 | Bonutti |
| 7,881,768 B2 | 2/2011 | Lang et al. |
| 7,914,533 B2 | 3/2011 | Nelson et al. |
| 7,981,158 B2 | 7/2011 | Fitz et al. |
| 7,983,777 B2 | 7/2011 | Melton et al. |
| 8,036,729 B2 | 10/2011 | Lang et al. |
| 8,062,302 B2 | 11/2011 | Lang et al. |
| 8,066,708 B2 | 11/2011 | Lang et al. |
| 8,083,745 B2 | 12/2011 | Lang et al. |
| 8,105,330 B2 | 1/2012 | Fitz et al. |
| 8,112,142 B2 | 2/2012 | Alexander et al. |
| 8,122,592 B2 | 2/2012 | Burdulis, Jr. et al. |
| RE43,282 E | 3/2012 | Alexander et al. |
| 8,236,016 B2 * | 8/2012 | To ............... A61B 17/320758 606/159 |
| 8,430,879 B2 | 4/2013 | Stoneburner et al. |
| 8,496,663 B2 | 7/2013 | White et al. |
| 8,535,319 B2 | 9/2013 | Ball |
| 8,579,980 B2 | 11/2013 | Delurio et al. |
| 8,636,744 B2 | 1/2014 | Tochigi et al. |
| 8,715,362 B2 | 5/2014 | Reiley et al. |
| 8,808,297 B2 | 8/2014 | Stemniski |
| 8,808,303 B2 | 8/2014 | Stemniski |
| 9,005,255 B2 | 4/2015 | Lewis et al. |
| 9,017,334 B2 | 4/2015 | Carroll et al. |
| 9,125,674 B2 | 9/2015 | White et al. |
| 9,128,627 B1 | 9/2015 | Bachu et al. |
| 9,259,250 B2 | 2/2016 | Saravia et al. |
| 9,265,511 B2 | 2/2016 | White et al. |
| 9,351,739 B2 | 5/2016 | Mahoney et al. |
| 9,402,640 B2 | 8/2016 | Stemniski et al. |
| 9,672,607 B2 | 6/2017 | Demri et al. |
| 9,675,365 B2 | 6/2017 | Lancianese et al. |
| 10,105,168 B2 | 10/2018 | Blau |
| 10,130,430 B2 | 11/2018 | Kao et al. |
| 10,315,007 B2 * | 6/2019 | Chan ............... A61M 25/0105 |
| 10,390,842 B2 | 8/2019 | Sander |
| 10,413,308 B2 | 9/2019 | Stemniski et al. |
| 10,433,911 B2 | 10/2019 | Wang et al. |
| 10,456,179 B2 | 10/2019 | Luna et al. |
| 10,667,867 B2 | 6/2020 | Ashish et al. |
| 10,835,265 B2 | 11/2020 | White et al. |
| 10,835,266 B2 | 11/2020 | White et al. |
| 11,134,964 B2 | 10/2021 | Free et al. |
| 11,147,627 B2 | 10/2021 | Gangwar et al. |
| 11,172,945 B1 | 11/2021 | Lian |
| 2001/0001120 A1 | 5/2001 | Masini |
| 2001/0010023 A1 | 7/2001 | Schwartz et al. |
| 2001/0039455 A1 | 11/2001 | Simon et al. |
| 2002/0013626 A1 | 1/2002 | Geislich et al. |
| 2002/0029038 A1 | 3/2002 | Haines |
| 2002/0045940 A1 | 4/2002 | Giannelli et al. |
| 2002/0059049 A1 | 5/2002 | Bradbury et al. |
| 2002/0068979 A1 | 6/2002 | Brown et al. |

(56) References Cited

U.S. PATENT DOCUMENTS

| | | |
|---|---|---|
| 2002/0072821 A1 | 6/2002 | Baker |
| 2002/0079601 A1 | 6/2002 | Russell et al. |
| 2002/0082703 A1 | 6/2002 | Repicci |
| 2002/0087274 A1 | 7/2002 | Alexander et al. |
| 2002/0106625 A1 | 8/2002 | Hung et al. |
| 2002/0115647 A1 | 8/2002 | Halvorsen et al. |
| 2002/0120274 A1 | 8/2002 | Overaker et al. |
| 2002/0120281 A1 | 8/2002 | Overaker |
| 2002/0123817 A1 | 9/2002 | Clasbrummel et al. |
| 2002/0127264 A1 | 9/2002 | Felt et al. |
| 2002/0133230 A1 | 9/2002 | Repicci |
| 2002/0143402 A1 | 10/2002 | Steinberg |
| 2002/0151986 A1 | 10/2002 | Asculai et al. |
| 2002/0156150 A1 | 10/2002 | Asculai et al. |
| 2002/0156479 A1 | 10/2002 | Schulzki et al. |
| 2002/0173852 A1 | 11/2002 | Felt et al. |
| 2002/0183850 A1 | 12/2002 | Felt et al. |
| 2002/0198531 A1 | 12/2002 | Millard et al. |
| 2003/0028196 A1 | 2/2003 | Bonutti |
| 2003/0055500 A1 | 3/2003 | Fell et al. |
| 2003/0055501 A1 | 3/2003 | Fell et al. |
| 2003/0055502 A1 | 3/2003 | Lang et al. |
| 2003/0060882 A1 | 3/2003 | Fell et al. |
| 2003/0060883 A1 | 3/2003 | Fell et al. |
| 2003/0060884 A1 | 3/2003 | Fell et al. |
| 2003/0060885 A1 | 3/2003 | Fell et al. |
| 2003/0100907 A1 | 5/2003 | Rosa et al. |
| 2003/0100953 A1 | 5/2003 | Rosa et al. |
| 2003/0120347 A1 | 6/2003 | Steinberg |
| 2003/0158558 A1 | 8/2003 | Horn |
| 2003/0158606 A1 | 8/2003 | Coon et al. |
| 2003/0163137 A1 | 8/2003 | Smucker et al. |
| 2003/0173695 A1 | 9/2003 | Monkhouse et al. |
| 2003/0216669 A1 | 11/2003 | Lang et al. |
| 2003/0220641 A1* | 11/2003 | Thelen ............... A61B 17/8805 606/60 |
| 2003/0225457 A1 | 12/2003 | Justin et al. |
| 2003/0236521 A1 | 12/2003 | Brown et al. |
| 2003/0236526 A1 | 12/2003 | Van Hoeck et al. |
| 2004/0098133 A1 | 5/2004 | Carignan et al. |
| 2004/0102852 A1 | 5/2004 | Johnson et al. |
| 2004/0122521 A1 | 6/2004 | Lee et al. |
| 2004/0133276 A1 | 7/2004 | Lang et al. |
| 2004/0138754 A1 | 7/2004 | Lang et al. |
| 2004/0147927 A1 | 7/2004 | Tsougarakis et al. |
| 2004/0153079 A1 | 8/2004 | Tsougarakis et al. |
| 2004/0153162 A1 | 8/2004 | Sanford et al. |
| 2004/0153164 A1 | 8/2004 | Sanford et al. |
| 2004/0167390 A1 | 8/2004 | Alexander et al. |
| 2004/0167630 A1 | 8/2004 | Rolston |
| 2004/0193268 A1 | 9/2004 | Hazebrouck et al. |
| 2004/0193280 A1 | 9/2004 | Webster et al. |
| 2004/0199166 A1 | 10/2004 | Schmieding et al. |
| 2004/0204644 A1 | 10/2004 | Tsougarakis et al. |
| 2004/0204760 A1 | 10/2004 | Fitz et al. |
| 2004/0236424 A1 | 11/2004 | Berez et al. |
| 2004/0249386 A1 | 12/2004 | Faoro |
| 2005/0015153 A1 | 1/2005 | Goble et al. |
| 2005/0021039 A1 | 1/2005 | Cusick et al. |
| 2005/0043807 A1 | 2/2005 | Wood |
| 2005/0049603 A1 | 3/2005 | Calton et al. |
| 2005/0055028 A1 | 3/2005 | Haines |
| 2005/0085920 A1 | 4/2005 | Williamson |
| 2005/0107883 A1 | 5/2005 | Goodfried et al. |
| 2005/0107884 A1 | 5/2005 | Johnson et al. |
| 2005/0119664 A1 | 6/2005 | Carignan et al. |
| 2005/0143745 A1 | 6/2005 | Hodorek et al. |
| 2005/0148843 A1 | 7/2005 | Roose |
| 2005/0171545 A1 | 8/2005 | Walsh et al. |
| 2005/0171612 A1 | 8/2005 | Rolston |
| 2005/0187555 A1 | 8/2005 | Biedermann et al. |
| 2005/0192588 A1 | 9/2005 | Garcia |
| 2005/0216305 A1 | 9/2005 | Funderud |
| 2005/0234461 A1 | 10/2005 | Burdulis et al. |
| 2005/0267584 A1 | 12/2005 | Burdulis et al. |
| 2005/0288792 A1 | 12/2005 | Landes et al. |
| 2006/0052795 A1 | 3/2006 | Burdulis et al. |
| 2006/0111722 A1 | 5/2006 | Bouadi |
| 2006/0149283 A1 | 7/2006 | May et al. |
| 2006/0200162 A1 | 9/2006 | Farling et al. |
| 2006/0235421 A1 | 10/2006 | Rosa et al. |
| 2007/0015995 A1 | 1/2007 | Lang |
| 2007/0073305 A1 | 3/2007 | Lionberger et al. |
| 2007/0118141 A1 | 5/2007 | Marchyn et al. |
| 2007/0129808 A1 | 6/2007 | Justin et al. |
| 2007/0150065 A1 | 6/2007 | Angibaud |
| 2007/0162025 A1 | 7/2007 | Tornier et al. |
| 2007/0198022 A1 | 8/2007 | Lang et al. |
| 2007/0203430 A1 | 8/2007 | Lang et al. |
| 2007/0203455 A1 | 8/2007 | Tremaglio et al. |
| 2007/0233128 A1 | 10/2007 | Schmieding et al. |
| 2007/0233151 A1 | 10/2007 | Chudik |
| 2007/0233156 A1 | 10/2007 | Metzger |
| 2007/0276224 A1 | 11/2007 | Lang et al. |
| 2007/0293868 A1 | 12/2007 | Delfosse et al. |
| 2008/0004709 A1 | 1/2008 | O'Neill et al. |
| 2008/0015433 A1 | 1/2008 | Alexander et al. |
| 2008/0025463 A1 | 1/2008 | Lang et al. |
| 2008/0031412 A1 | 2/2008 | Delfosse et al. |
| 2008/0058613 A1 | 3/2008 | Lang et al. |
| 2008/0058945 A1 | 3/2008 | Hajaj et al. |
| 2008/0114370 A1 | 5/2008 | Schoenefeld |
| 2008/0170659 A1 | 7/2008 | Lang et al. |
| 2008/0195109 A1 | 8/2008 | Hunter et al. |
| 2008/0195216 A1 | 8/2008 | Lang |
| 2008/0219412 A1 | 9/2008 | Lang |
| 2008/0243127 A1 | 10/2008 | Lang |
| 2008/0255565 A1 | 10/2008 | Fletcher |
| 2008/0275452 A1 | 11/2008 | Lang et al. |
| 2008/0281328 A1 | 11/2008 | Lang et al. |
| 2008/0281329 A1 | 11/2008 | Lang et al. |
| 2008/0281426 A1 | 11/2008 | Fitz et al. |
| 2008/0287953 A1 | 11/2008 | Sers |
| 2008/0306605 A1 | 12/2008 | Hasselman |
| 2009/0024131 A1 | 1/2009 | Metzger et al. |
| 2009/0043310 A1 | 2/2009 | Rasmussen |
| 2009/0076371 A1 | 3/2009 | Lang et al. |
| 2009/0087276 A1 | 4/2009 | Rose |
| 2009/0088753 A1 | 4/2009 | Aram et al. |
| 2009/0088758 A1 | 4/2009 | Bennett |
| 2009/0099567 A1 | 4/2009 | Zajac |
| 2009/0131941 A1 | 5/2009 | Park et al. |
| 2009/0131942 A1 | 5/2009 | Aker et al. |
| 2009/0149964 A1 | 6/2009 | May et al. |
| 2009/0198244 A1 | 8/2009 | Leibel |
| 2009/0204115 A1 | 8/2009 | Dees et al. |
| 2009/0222014 A1 | 9/2009 | Bojarski et al. |
| 2009/0307893 A1 | 12/2009 | Bojarski et al. |
| 2010/0057133 A1 | 3/2010 | Simon |
| 2010/0076441 A1 | 3/2010 | May et al. |
| 2010/0121326 A1 | 5/2010 | Woll et al. |
| 2010/0160917 A1 | 6/2010 | Fitz et al. |
| 2010/0262150 A1 | 10/2010 | Lian |
| 2010/0274251 A1 | 10/2010 | Ranft |
| 2010/0281678 A1 | 11/2010 | Burdulis, Jr. et al. |
| 2010/0298894 A1 | 11/2010 | Bojarski et al. |
| 2010/0305573 A1 | 12/2010 | Fitz et al. |
| 2010/0305574 A1 | 12/2010 | Fitz et al. |
| 2011/0066193 A1 | 3/2011 | Lang et al. |
| 2011/0071581 A1 | 3/2011 | Lang et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0218539 A1 | 9/2011 | Fitz et al. |
| 2011/0218542 A1 | 9/2011 | Lian et al. |
| 2011/0218584 A1 | 9/2011 | Fitz et al. |
| 2011/0230888 A1 | 9/2011 | Lang et al. |
| 2011/0238073 A1 | 9/2011 | Lang et al. |

(56) References Cited

U.S. PATENT DOCUMENTS

| | | |
|---|---|---|
| 2011/0313423 A1 | 12/2011 | Lang et al. |
| 2011/0319897 A1 | 12/2011 | Lang et al. |
| 2011/0319900 A1 | 12/2011 | Lang et al. |
| 2012/0010719 A1 | 1/2012 | Reiley |
| 2012/0029520 A1 | 2/2012 | Lang et al. |
| 2012/0041446 A1 | 2/2012 | Wong et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0101503 A1 | 4/2012 | Lang et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2013/0261628 A1 | 10/2013 | Burley et al. |
| 2014/0020690 A1 | 1/2014 | Triplett |
| 2014/0270065 A1 | 9/2014 | Aram et al. |
| 2014/0275955 A1 | 9/2014 | Crawford et al. |
| 2014/0276853 A1 | 9/2014 | Long et al. |
| 2014/0277538 A1 | 9/2014 | Sander |
| 2015/0051696 A1* | 2/2015 | Hou .................. A61M 25/0905 623/2.11 |
| 2015/0134071 A1 | 5/2015 | Luna et al. |
| 2015/0320567 A1 | 11/2015 | Terrill et al. |
| 2016/0022283 A1 | 1/2016 | Wallace et al. |
| 2016/0051369 A1 | 2/2016 | Sander |
| 2016/0262903 A1 | 9/2016 | West |
| 2016/0310193 A1 | 10/2016 | Lv et al. |
| 2017/0224383 A1 | 8/2017 | Wong |
| 2018/0055648 A1 | 3/2018 | Dhillon et al. |
| 2018/0303490 A1 | 10/2018 | Loring et al. |
| 2019/0070012 A1 | 3/2019 | Leemrijse et al. |
| 2019/0209080 A1 | 7/2019 | Gullotti et al. |
| 2020/0015867 A1 | 1/2020 | Luna et al. |
| 2020/0113712 A1 | 4/2020 | Luna et al. |
| 2020/0330238 A1 | 10/2020 | Calamel et al. |
| 2020/0337850 A1 | 10/2020 | Reiley |
| 2021/0378753 A1 | 12/2021 | Christen et al. |
| 2022/0280307 A1 | 9/2022 | Haddad et al. |
| 2022/0316504 A1 | 10/2022 | Kubacki |

FOREIGN PATENT DOCUMENTS

| | | |
|---|---|---|
| DE | 2306552 | 8/1974 |
| DE | 3516743 | 11/1986 |
| DE | 44 34 539 | 4/1996 |
| DE | 19501069 | 7/1996 |
| DE | 20303498 | 8/2003 |
| DE | 202008017199 | 3/2009 |
| DE | 202008017200 | 3/2009 |
| EP | 0377901 | 10/1989 |
| EP | 0528080 | 2/1993 |
| EP | 0530804 | 10/1993 |
| EP | 0626156 | 11/1994 |
| EP | 0704193 | 4/1996 |
| EP | 0896825 | 2/1999 |
| EP | 0938869 | 9/1999 |
| EP | 0613380 | 12/1999 |
| EP | 0993807 | 4/2000 |
| EP | 1074229 | 2/2001 |
| EP | 1077253 | 2/2001 |
| EP | 1120087 | 8/2001 |
| EP | 1129675 | 9/2001 |
| EP | 1132061 | 9/2001 |
| EP | 0732091 | 12/2001 |
| EP | 0814731 | 8/2002 |
| EP | 1234552 | 8/2002 |
| EP | 1234555 | 8/2002 |
| EP | 0809987 | 10/2002 |
| EP | 0833620 | 10/2002 |
| EP | 2124832 | 12/2009 |
| FR | 2819714 | 7/2002 |
| GB | 1451283 | 9/1976 |
| GB | 2291355 | 1/1996 |
| GB | 2348373 | 10/2000 |
| JP | 8-173465 | 7/1996 |
| JP | 9-206322 | 8/1997 |
| JP | 2000093435 | 4/2000 |
| JP | 2002-102236 | 4/2002 |
| JP | 2008-537689 | 9/2008 |
| JP | 2009515610 | 4/2009 |
| WO | WO 87/02882 | 5/1987 |
| WO | WO 90/009769 | 9/1990 |
| WO | WO 93/004710 | 3/1993 |
| WO | WO 93/009819 | 5/1993 |
| WO | WO 93/025157 | 12/1993 |
| WO | WO 95/027450 | 10/1995 |
| WO | WO 95/028688 | 10/1995 |
| WO | WO 95/030390 | 11/1995 |
| WO | WO 95/032623 | 12/1995 |
| WO | WO 96/024302 | 8/1996 |
| WO | WO 97/025942 | 7/1997 |
| WO | WO 97/026847 | 7/1997 |
| WO | WO 97/027885 | 8/1997 |
| WO | WO 97/038676 | 10/1997 |
| WO | WO 98/012994 | 4/1998 |
| WO | WO 98/20816 | 5/1998 |
| WO | WO 98/030617 | 7/1998 |
| WO | WO 98/32384 | 7/1998 |
| WO | WO 99/002654 | 1/1999 |
| WO | WO 99/008598 | 2/1999 |
| WO | WO 99/008728 | 2/1999 |
| WO | WO 99/042061 | 8/1999 |
| WO | WO 99/047186 | 9/1999 |
| WO | WO 99/051719 | 10/1999 |
| WO | WO 99/056674 | 11/1999 |
| WO | WO 00/009179 | 2/2000 |
| WO | WO 00/015153 | 3/2000 |
| WO | WO 00/035346 | 6/2000 |
| WO | WO 00/048550 | 8/2000 |
| WO | WO 00/059411 | 10/2000 |
| WO | WO 00/074554 | 12/2000 |
| WO | WO 01/010356 | 2/2001 |
| WO | WO 01/017463 | 3/2001 |
| WO | WO 01/019254 | 3/2001 |
| WO | WO 01/035968 | 5/2001 |
| WO | WO 01/045764 | 6/2001 |
| WO | WO 01/068800 | 9/2001 |
| WO | WO 01/070142 | 9/2001 |
| WO | WO 01/091672 | 12/2001 |
| WO | WO 02/000270 | 1/2002 |
| WO | WO 02/000275 | 1/2002 |
| WO | WO 02/002158 | 1/2002 |
| WO | WO 02/022013 | 3/2002 |
| WO | WO 02/022014 | 3/2002 |
| WO | WO 02/023483 | 3/2002 |
| WO | WO 02/034310 | 5/2002 |
| WO | WO 02/036147 | 5/2002 |
| WO | WO 02/096268 | 12/2002 |
| WO | WO 03/007788 | 1/2003 |
| WO | WO 03/037192 | 5/2003 |
| WO | WO 03/047470 | 6/2003 |
| WO | WO 03/051210 | 6/2003 |
| WO | WO 03/055400 | 7/2003 |
| WO | WO 2003/065907 | 8/2003 |
| WO | WO 04/043305 | 5/2004 |
| WO | WO 04/049981 | 6/2004 |
| WO | WO 05/051239 | 6/2005 |
| WO | WO 05/051240 | 6/2005 |
| WO | WO 06/060795 | 6/2006 |
| WO | WO 06/127283 | 11/2006 |
| WO | WO 07/041375 | 4/2007 |
| WO | WO 2007/061983 | 5/2007 |
| WO | WO 07/092841 | 8/2007 |
| WO | WO 08/112996 | 9/2008 |
| WO | WO 08/157412 | 12/2008 |
| WO | WO 2009/001083 | 12/2008 |
| WO | WO 09/111639 | 9/2009 |
| WO | WO2009143374 | 11/2009 |
| WO | WO2009158522 | 12/2009 |
| WO | WO 2010/099142 | 9/2010 |
| WO | WO 2010/120346 | 10/2010 |

(56) References Cited

FOREIGN PATENT DOCUMENTS

| WO | WO 2010/121147 | 10/2010 |
|---|---|---|
| WO | WO2010135156 | 11/2010 |
| WO | WO 2011/110374 | 9/2011 |
| WO | WO2012121726 | 9/2012 |
| WO | WO2014020561 | 2/2014 |
| WO | 2019009891 A1 | 1/2019 |
| WO | 2019094361 A1 | 5/2019 |
| WO | WO2020124047 | 6/2020 |
| WO | WO 2020124052 | 6/2020 |
| WO | WO 2020242542 | 12/2020 |
| WO | WO 2022015877 | 1/2022 |
| WO | WO 2022094052 | 5/2022 |

OTHER PUBLICATIONS

Andersson, et al., "Macintosh Arthroplasty In Rheumatoid Arthritis," Acta. Orthrop. Scand., 1974, pp. 245-259, 45(2).
Anonymous: "Angle bracket (fastener)—Wikipedia", May 22, 2021, 1 page.
Anonymous: "Light Tube—Wikipedia", Mar. 4, 2021, 11 pages.
Anonymous: Newtonian Telescope—Wikipedia, May 23, 2021, 6 pages.
Argenson, et al., "Is There a Place for Patellofemoral Arthroplasty? ," Clinical Orthopaedics and Related Research No. 321, 1995, pp. 162-167.
Birnbaum, et al., "Computer-Assisted Orthopedic Surgery with Individual Templates and Comparison to Conventional Operation Method," Spine, Feb. 2001, pp. 365-369, vol. 26, No. 4.
Chelule, et al., "Computer Aided Design of Personalized Jigs in Total Knee Replacement," 3rd Annual Meeting of CAOS Int'l Proc., Jun. 18-21, 2003, pp. 58-59, Spain.
Dare, S., Bobyn, J., Drouin, G., Dussault, R., Gariepy, R., "Use of Computerized Tomography and Numerical Control Machining for the Fabrication of Custom Arthroplasty Prostheses." Second World Congress on Biomaterials, 10th Annual Meeting of the Society for Biomaterials, p. 233, Washington, D.C., Apr. 27-May 1, 1984.
DePuy Synthes, "Flexible Reamers for Intramedullary Nails" Surgical Technique, 22 pages, 2017.
De Winter, et al., "The Richards Type II Patellofemoral Arthroplasty," Acta Orthop Scand, 2001, pp. 487-490, 72(5).
Delp, et al., "A Graphics-Based Software System to Develop and Analyze Models of Musculoskeletal Structures," Comput. Biol. Med., 1995, pp. 21-34, vol. 25, No. 1.
Farrar, et al., "Computed Tomography Scan Scout Film for Measurement of Femoral Axis in Knee Arthroplasty," J. Arthroplasty, 1999, pp. 1030-1031, vol. 14, No. 8.
U.S. Appl. No. 13/465,547, dated Feb. 26, 2014.
First Office Action for Japanese Patent Appln. No. 2011-552091, dated Oct. 25, 2013.
Froemel, et al., "Computer Assisted Template Based Navigation for Total Knee Replacement," Documents presented at CAOS on Jun. 17, 2001, 4 pages.
Hafez, et al., "Computer Assisted Total Knee Replacement: Could a Two-Piece Custom Template Replace the Complex Conventional Instrumentations?", 4th Annual Meeting of CAOS Int'l Proc., Jun. 16-19, 2004, pp. 63-64, Chicago.
Hafez, et al., "Computer-Assisted Total Hip Arthroplasty: The Present and the Future," Future Rheumatol., 2006, pp. 121-131, vol. 1.
Kim, et al., "Measurement of Femoral Neck Anteversion in 3D. Part 1: 3D Imaging Method," Med. and Biol. Eng. and Computing, 2000, pp. 603-609, vol. 38, No. 6.
Lam, et al., "X-Ray Diagnosis: A Physician's Approach," 1998, Title page and Table of Contents pages Only, ISBN 9813083247, Springer-Verlag publishers.
Lam et al . . . "VarusNalgus Alignment of the Femoral Component in Total Knee Arthroplasty," The Knee, 2003, pp. 237-241, vol. 10.
Lu, et al., "In Vitro Degradation of Porous poly(L-lactic acid) Foams," Biomaterials, Aug. 2000, pp. 1595-1605, 21(15).

Mahaisavariya, et al., "Morphological Study of the Proximal Femur: a New Method of Geometrical Assessment Using 3-Dimensional Reverse Engineering", Medical Engineering & Physics 24 (2002) pp. 617-622.
Marler, et al., "Soft-Tissue Augmentation with Injectable Alginate and Synegeneic Fibroblasts," Plastic & Reconstructive Surgery, May 2000 pp. 2049-2058, 105(6).
PCT/US2010/025143, International Preliminary Report on Patentability and Written Opinion, Sep. 9, 2011.
Portheine, et al., "Potentials of CT-based Planning and Template-based Procedure in Hip and Knee Surgery," Orth. Prac., 2000, pp. 786-791, vol. 36, English Translation with Certification.
Radermacher, "Computer Assisted Matching of Planning and Execution in Orthopedic Surgery," Slide Presentation, Nov. 29, 1993, 22 pages.
Radermacher, "Template Based Navigation—An Efficient Technique for Hip and Knee Surgery," CAOS First Asian Meet, Mar. 27-28, 2004, pp. 45-50, India.
Radermacher, et al., "Computer-Assisted Planning and Operation in Orthopedics," Orth. Prac. 36th Year, Dec. 2000, pp. 731-737, English Translation with Certification.
Rau, et al., "Small and Neat," Medical Tech. Int'l, 1993-94, pp. 65, 67 and 69.
Schkommadau, et al., "Clinical Experience With the Individual Template Technique," Orth. Prac., 2001, pp. 19-22, vol. 37, No. 1, English Translation with Certification.
Seel, et al., "Three-Dimensional Planning and Virtual Radiographs in Revision Total Hip Arthroplasty for Instability," Clinical Orthopaedics and Related Research, Jan. 2006, pp. 35-38, No. 442.
Slone, et al., "Body CT: a Practical Approach," 1999, Title page and Table of Contents pages Only, ISBN 007058219, McGraw-Hill.
Staudte, et al., "Computer-Assisted Operation Planning and Technique in Orthopedics," North Rhine-Westphalia Acad. for Sciences, Lecture N.444, 2000, 17 pages, ISSN 0944-8799, in German.
Staudte, et al., "Computer-Assisted Operation Planning and Technique in Orthopedics," North Rhine-Westphalia Acad. for Sciences, Lecture N.444, 2000, 34 pages, ISSN 0944-8799, English Translation with Certification.
Stauffer, et al., "The Macintosh Prosthesis. Prospective Clinical and Gait Evaluation," Arch. Surg., 1975, pp. 717-720, 110(6).
Stout, et al., "X-RAY Structure Determination: A Practical Guide," 1989, Title page and Table of Contents pages Only, ISBN 0471607118, John Wiley & Sons.
Stryker Trauma GmbH, "Bixcut Reamer System" Osteosynthesis, 8 sheets, 2009.
Synthes, "SynReam, The Synthes Reaming System" Surgical Technique, 22 pages, 2005.
Tamez-Pena, et al., "MRIIsotropic Resolution Reconstruction from Two Orthogonal Scans," Proceedings of the SPIE—The International Society for Optical Engineering SOIE—OMT, 2001, pp. 87-97, vol. 4322.
Testi, et al., "Border Tracing Algorithm Implementation for the Femoral Geometry Reconstruction," Camp. Meth. and Programs in Biomed., 2001, pp. 175-182, vol. 65.
Vandeberg, et al., "Assessment of Knee Cartilage in Cadavers with Dual-Detector Spiral CT Arthrography and MR Imaging," Radiology, Feb. 2002, pp. 430-435, 222(2).
Wiese, et al., "Biomaterial Properties and Biocompatibility in Cell Culture of a Novel Self-Inflating Hydrogel Tissue Expander," J. Biomedical Materials Research Part A, Nov. 2000, pp. 179-188, 54(2).
Woolson, S., Fellingham, L., Dev, P., and Vassiliadis, A., "Three Dimensional Imaging of Bone from Analysis of Computed Tomography Data." Orthopedics, vol. 8, No. 10, pp. 1269-1273, Oct. 1985.
Yusof, et al., "Preparation and Characterization of Chitin Beads as a Wound Dressing Precursor," J. Biomedical Materials Research Part A, Oct. 2000, pp. 59-68, 54(1).
Examination Report issued in connection with corresponding Indian Patent Application No. 2004/KOLNP/2013, Nov. 27, 2018, 7 pages.
First Office Action issued in connection with corresponding Chinese Patent Application No. 201610973637.8, Nov. 28, 2018, 6 pages.

(56) References Cited

OTHER PUBLICATIONS

First Examination Repot issued in connection with corresponding Australian Patent Application No. 2018204063, Jul. 10, 2019, 2 pages.
Second Examination Report issued in connection with corresponding Australian Patent Application No. 2019261830, May 4, 2021, 9 pages.
First Examination Repot issued in connection with corresponding Australian Patent Application No. 201926183, Dec. 21, 2020, 4 pages.
International Search Report and Written Opinion issued in connection with International Patent Application No. PCT/US2022/070130, May 13, 2022, 17 pages.
Extended European Search Report issued in connection with European Patent Application No. 22172072, filed May 4, 2023, 25 pages.
Extended European Search Report issued in connection with European Patent Application No. 20913581.3, Oct. 16, 2023, 8 pages.

\* cited by examiner

GUIDANCE TOOLS, SYSTEMS, AND METHODS

CROSS-REFERENCE TO RELATED APPLICATIONS AND INCORPORATION BY REFERENCE

This application is a National Stage Application, filed under 35 U.S.C. 371, of International Patent Application No. PCT/US2020/065189, filed on Dec. 16, 2020, which claims priority to U.S. Provisional Patent Application No. 62/962, 610, filed on Jan. 17, 2020, the entireties of which are incorporated herein by reference. This application also incorporates by reference the entire disclosures of commonly assigned U.S. Pat. No. 8,808,303, entitled "Orthopedic Surgical Guide;" U.S. Pat. No. 9,675,365, entitled "System and Method for Anterior Approach for Installing Tibial Stem;" and U.S. Pat. No. 10,456,179, entitled "Intramedullary Ankle Technique and System."

FIELD OF DISCLOSURE

The disclosed systems and methods relate to surgical tools and methods. More particularly, the disclosed systems and methods relate to guiding a flexible reamer, including flexible reamer that may be used to form an intramedullary canal.

BACKGROUND

Many surgical procedures use rotating cutting tools, such as reamers, to form cavities or channels within bone. One example of such a surgical procedure is a total ankle replacement ("TAR") procedure in which an intramedullary channel may be formed in a tibia so that the tibia may receive a stem component. The intramedullary channel typically is formed along the mechanical axis of the tibia, and many conventional techniques require the violation of additional bones beyond the tibia (e.g., the talus and calcaneus) to form the intramedullary channel. One example of such a technique is disclosed in commonly assigned U.S. Pat. No. 8,808,303, which has been incorporated by reference above. Violating additional bones beyond the tibia may increase the length of the surgery and risk of infection or other complications.

SUMMARY

In some embodiments, a guidance tool includes a body having a length extending from a first end to a second end. The body includes a shape memory section along the length of the body. The shape memory section has a curved shape.

In some embodiments, a method includes inserting a first end of a guidance tool into an end of a bone; advancing the guidance tool into the bone until a shape memory section of the guidance tool is disposed adjacent to the end of the bone; cutting the guidance tool at a location between the shape memory section and a second end of the guidance tool; and advancing a cutting tool along the guidance tool to form a cavity in the bone. Cutting the guidance tool allows the shape memory section of the guidance tool to regain its programmed shape.

In some embodiments, a method includes coupling a fixture along a length of a bone such that a hole defined by the fixture is positioned adjacent to a side of the bone; inserting a guidance tool through the hole of the fixture and into the bone until the guidance tool extends along a length of the bone and a leading end of the guidance tool is exposed adjacent to an end of the bone; and advancing a cutting tool along the guidance tool to form a cavity in the bone.

DETAILED DESCRIPTION

Figure 1:
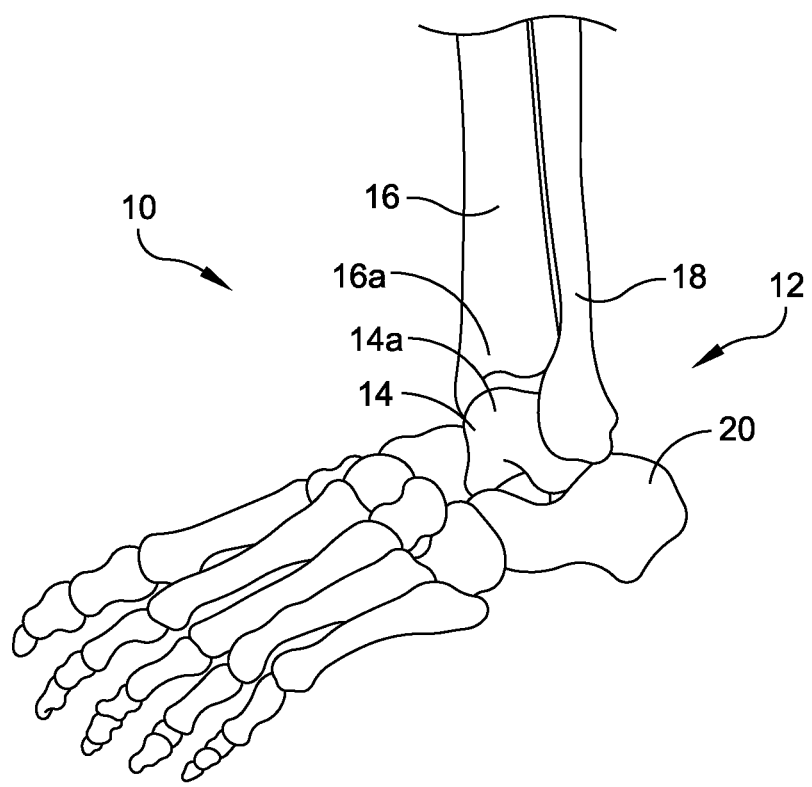
FIG. 1 illustrates one example of a human foot.

This description of preferred embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

The disclosed systems and methods advantageously facilitate the intramedullary guidance while minimizing and/or eliminating the violation of adjacent bones as is typically done during conventional surgical procedures. While the systems and methods are described in connection with performing TAR, one of ordinary skill in the art will understand that the disclosed systems and methods may be used to facilitate the creation of intramedullary canals or channels in other bones or body parts.

Figure 3:
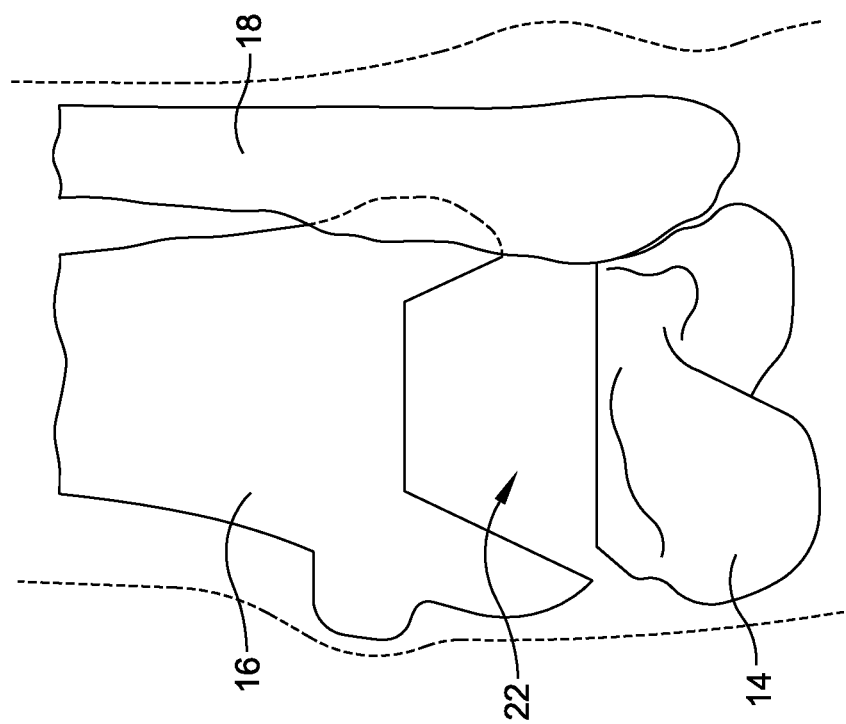
FIG. 3 illustrates one example of a resected tibia and a resected talus in accordance with some embodiments.
Figure 2:
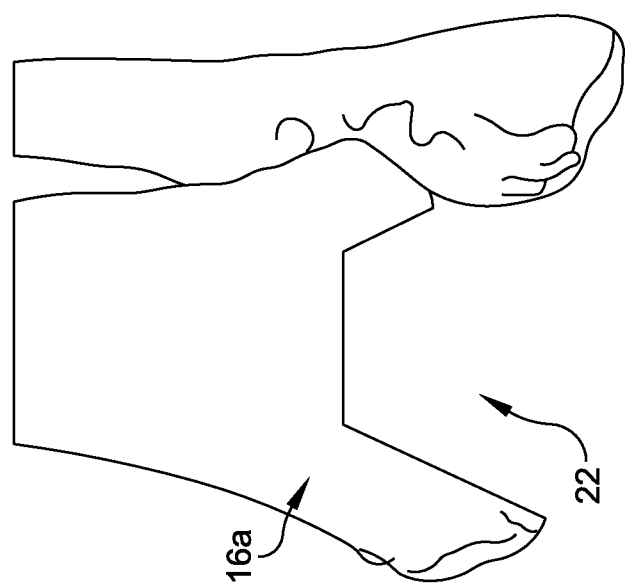
FIG. 2 illustrates one example of a resected tibia in accordance with some embodiments.

FIG. 1 illustrates one example of a human foot 10 and ankle 12. As is known, the human foot 10 includes a number of bones, including the talus 14, which sits atop the calcaneus 20. The talus 14 forms part of the ankle joint with the tibia 16, which is positioned adjacent to the fibula 18. To prepare an ankle 12 for a TAR, the talus 14 and tibia 16 may be resected to provide a resected joint space 22 as best seen in FIGS. 2 and 3. Examples of tools and procedures for forming the resected joint space 22 are disclosed in U.S. Pat. Nos. 8,808,303 and 9,675,365, which have been incorporated by reference above.

Figure 5:
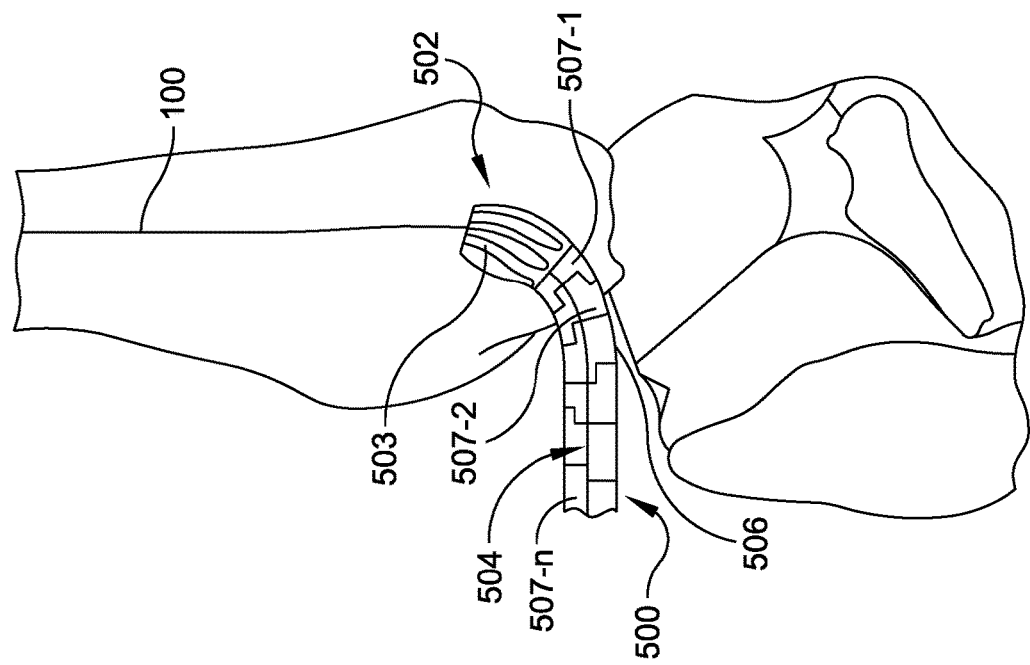
FIG. 5 is a sagittal plane view of a cutting tool being guided by the guidance tool shown in FIG. 4 in accordance with some embodiments.
Figure 4:
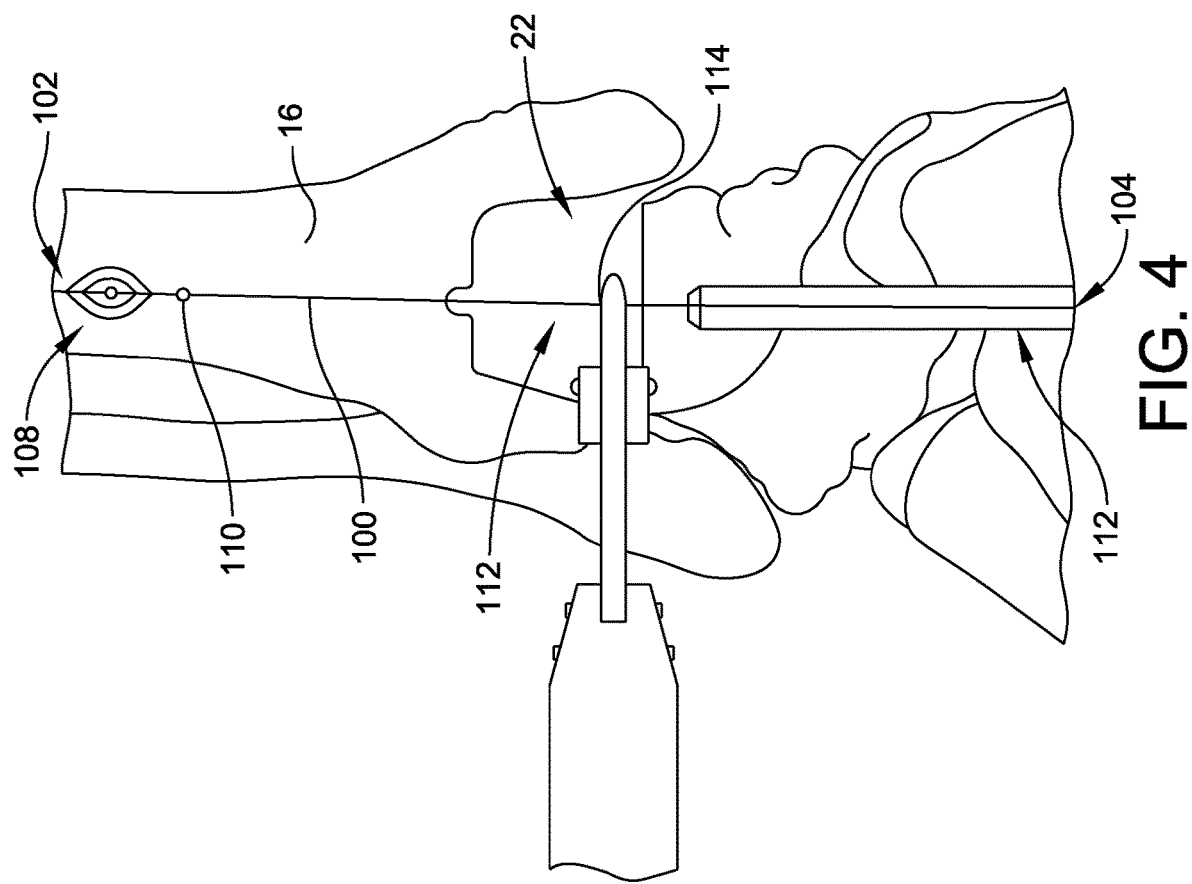
FIG. 4 is a frontal plane view of one example of a guidance tool being inserted into a tibia in accordance with some embodiments.

FIGS. 4 and 5 illustrate one example of a guidance tool in accordance with some embodiments. Guidance tool 100 has an elongate shape extending from a first end 102, which may be an insertion end, to a second end 104, which may be a trailing end. End 102 may include a point or taper for facilitating insertion of the guidance tool 100 into a medium, such as skin or bone. Guidance tool 100 may be formed from shape memory material, such as a shape memory alloy selected from the group consisting of Cu—Al—Ni, NiTi (e.g., Nitinol), Fe—Mn—Si, Cu—Zn—Al, and Cu—Al—Ni.

In some embodiments, guidance tool 100 may include a centering mechanism 108 for centering the guidance tool within a bone. For example, the centering mechanism 108 may include a balloon or stent material configured to expand from a first, collapsed configuration to a second, expanded configuration. The guidance tool 100 is inserted into the medium (e.g., an intramedullary space, such as cancellous bone) with the centering mechanism 108 in its collapsed configuration. When guidance tool 100 has been inserted to its desired depth or location, the centering mechanism 108 may be deployed into its expanded configuration.

As will be understood by one of ordinary skill in the art, the manner in which the centering mechanism 108 is deployed may vary. For example, in embodiments where the centering mechanism 108 includes a balloon, then a gas, gel, or liquid may be injected into the internal chamber defined by the balloon to increase the size of the balloon. Techniques similar to those used in vertebroplasty and kyphoplasty may be used to expand the balloon. One of ordinary skill in the art will understand that as the diameter of the balloon increases the cancellous bone is compressed against the stronger cortical bone thereby centering the guidance tool within the bone. Additional materials, such as a stent material, may be provided along with a balloon material to guide the expansion and shape of the balloon.

In some embodiments, guidance tool 100 includes a stop 110 along its length. For example, stop 110 may take the form of a bead, taper, or other protrusion having an enlarged diameter relative to one or more portions of guidance tool 100 that are adjacent to stop 110. Stop 110 may be disposed adjacent to centering mechanism 108 and is configured to stop the advancement of a cutting tool along the guidance tool 100, as will be described in greater detail below, thereby protecting the centering mechanism 108 from being damaged by the cutting tool.

Guidance tool 100 may include a shape memory section or portion 112. In some embodiments, the shape memory section 112 is curved to facilitate the guidance of a flexible cutting tool into an intramedullary canal. As described in greater detail below, the shape memory section 112 may be positioned along the length of the guidance tool 100 such that when the stop 110 is located at the desired location within the bone the shape memory section will be adjacent to an end of the bone.

In some embodiments, the guidance tool 100 may be placed within an inferior portion of a tibia 16 with the aid of a cannula. The tibia 16 and talus 14 may be prepared by making bony cuts, such as those described in U.S. Pat. No. 9,675,365, entitled "System and Method for Anterior Approach for Installing Tibial Stem," which is incorporated by reference herein in its entirety. Once the inferior portion of the tibia 16 is resected to form a resected joint space 22, the cannula may be positioned adjacent to the calcaneus 20.

With the cannula positioned, the leading end 102 of guidance tool 100 is inserted into the cannula and advanced into the calcaneus 20, talus 14, and tibia 16. The position of the guidance tool 100 within the tibia may be checked using fluoroscopy as will be understood by one of ordinary skill in the art. In some embodiments, the guidance tool 100 may include one or more markings (not shown) along its length. Each marking may identify a distance from the respective marking to the leading end 102 of the guidance tool 100 or a distance from the respective marking to the stop 110 such that a surgeon or physician will be able to determine if the guidance tool 100 has been inserted to the desired depth without the use of fluoroscopy.

In embodiments in which the guidance tool 100 is configured with a centering mechanism 108, the centering mechanism may be activated or deployed to center the guidance tool 100 within the tibia 16. For example, if the centering mechanism 108 includes a balloon that may be inflated around the guidance tool 100, then the balloon is inflated, such as by injecting a gas, gel, or liquid into the internal chamber defined by the balloon. As the balloon is filled, the balloon expands, which results in the cancellous being compressed. The cancellous bone is compressed to the stronger cortical bone which is sufficiently strong to withstand the pressure exerted by the balloon being inflated.

With the guidance tool 100 positioned within the tibia 16, the shape memory section 112 may be deployed. In some embodiments, the shape memory section 112 is deployed by cutting the guidance tool 100, such as by using a pin cutter, adjacent to the shape memory section 112 to form a cut end 114. The cutting of the guidance tool 100 eliminates the straightening force that was being applied to the guidance tool 100 by the cannula such that the shape memory section 112 is now free to revert back to its programmed shape, which may be a curved shape. In some embodiments, the curved shape of the shape memory section 112 extends through the anterior window of the resected joint space 22. In some embodiments, the shape memory section 112 may be deployed prior to positioning the cannula and activating or deploying the centering mechanism as will be understood by one of ordinary skill in the art.

The guidance tool 100 is now ready to guide a cutting tool, such as a flexible reamer 500, to prepare an intramedullary channel for receiving an implant. In some embodiments, a flexible reamer, such as the flexible reamer 500 described in U.S. Pat. No. 10,456,179, entitled "Intramedullary Ankle Technique and System," the entirety of which is incorporated by reference herein, is modified to provide a cannulated flexible reamer. The cannulated flexible reamer 500 defines a passageway 504 that extends through the nose 502 and the rest of the reamer 500. In some embodiments, the body 506 of the cannulated flexible reamer 500 includes a plurality of segments. The segments 507-1, 507-2, . . . 507-n (collectively, "segments 507") may be movable (e.g., rotatable and/or pivotable) relative to an adjacent segment 507. In some embodiment, each segment 507 is movable (e.g., rotatable and/or pivotable) relative to an adjacent segment such that the reamer 500 may bend along its length.

The cannulated flexible reamer 500 is inserted over the guidance tool 100. More particularly, the leading end or nose 502 of the cannulated flexible reamer 500, which may include one or more flutes or cutting surfaces 503, is slid onto the cut end 114 of guidance tool 100 such that the guidance tool 100 is received within passageway 504 of reamer 500 as shown in FIG. 5. The flexible reamer 500 is advanced along the guidance tool 100, including along the shape memory section 112, and up into the tibia 16 to form an intramedullary channel. The flexible reamer is advanced along the length of the guidance tool 100 until it contacts stop 110 or till a desired depth has been achieved. In some embodiments, the guidance tool 100 may include markings along its length to provide a visual aid to the surgeon.

Once the intramedullary channel has been formed, the cannulated flexible reamer 500 may be slid off the guidance tool 100. The guidance tool 100 may then be removed from the tibia 16. In some embodiments in which the guidance tool 100 includes a centering mechanism 108 in the form of a balloon, the balloon may be deflated prior to removing the guidance tool 100 from its placement within the tibia 16.

Figure 7:
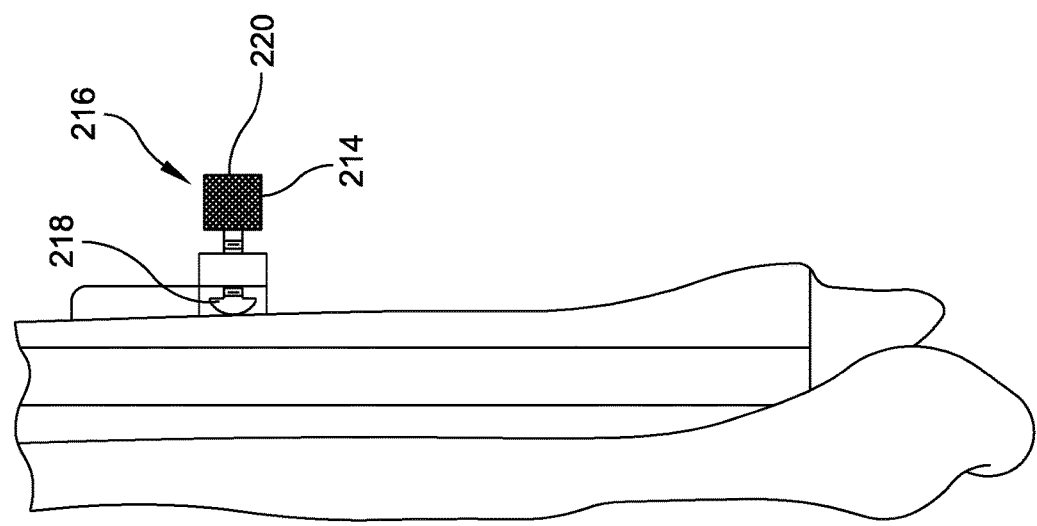
FIG. 7 is a sagittal plane view of the fixture illustrated in FIG. 6 in accordance with some embodiments.
Figure 6:
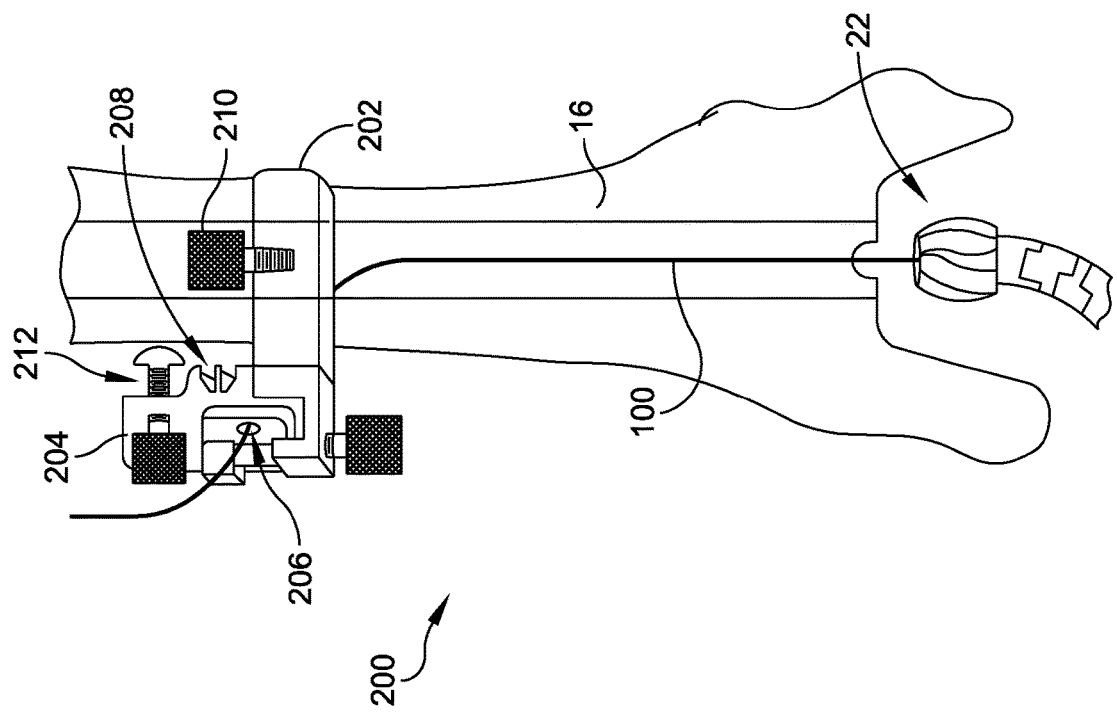
FIG. 6 is a frontal plane view of one example of a fixture and guidance tool in accordance with some embodiments.

FIGS. 6 and 7 illustrate another example of the insertion of a guidance tool into a bone canal in accordance with some embodiments. As shown in FIGS. 6 and 7, the guidance tool 100 is inserted into the bone canal with the assistance of a fixture 200. Fixture 200 may include a body 202 that may be coupled to the bone or to an extramedullary guidance device, such as, for example, a foot holder and alignment tool 300 described in U.S. Pat. No. 8,808,303, as will be understood by one of ordinary skill in the art.

In some embodiments, body 202 is sized and configured such that the length of the body 202 extends across or substantially across a width of a bone, such as a human tibia 16. Body 202 of fixture 200 may include a flange 204 extending at an angle (e.g., perpendicularly) with respect to a longitudinal axis defined by the body 202. Body 202 defines at least one hole 206 sized and configured to receive a guidance tool, such as guidance tool 100 described above or a conventional k-wire. In some embodiments, hole 206 is configured to allow the guidance tool to be inserted at a non-orthogonal angle relative to an axis defined by the bone (e.g., a mechanical axis or a longitudinal axis). Body 202 may also include one or more gunsights 208 for providing an alignment check.

Body 202 may also include one or more adjustment mechanisms, including an anterior-posterior ("AP") adjustment block 210, a medial-lateral ("ML") adjustment block 212, and a proximal-distal adjustment block 214. The implementation of the adjustment mechanisms may be varied. For example, in some embodiments, the adjustment mechanisms include a threaded thumb screw 216 having an enlarged foot 218 that is disposed at an opposite end of thumb wheel 220. In some embodiments, the foot 218 is sized and configured to contact, but not cause damage or dig into, a bone, body 202 of fixture 200, or the extramedullary guidance tool 100 as will be understood by one of ordinary skill in the art.

In use, the fixture 200 is positioned along a length of a bone, such as a tibia 16, after the bone has been prepared to accept a guidance tool 100. For example, in embodiments in which the fixture 200 and guidance tool 100 are to be used to guide a flexible reamer, e.g., flexible reamer 500, to form an intramedullary channel for receiving a tibial component of an ankle prosthesis, the inferior portion 16a of the tibia 16 is resected to form a resected joint space 22 as shown in FIGS. 2 and 3. The resected joint space may be formed as described in U.S. Pat. No. 9,675,365, entitled "System and Method for Anterior Approach for Installing Tibial Stem," which has been incorporated by reference above.

The fixture 200 may be positioned along the length of the bone by using a strap (not shown) to couple the fixture 200 directly to the bone or by coupling the fixture 200 to an external guidance device (also not shown). Positioning of the fixture 200 along the length of the bone may also include adjusting the location of the fixture 200 using one or more of the adjustment mechanisms, i.e., AP adjustment block 210, ML adjustment block 212, and proximal-distal adjustment block 214. The adjustment mechanisms may be used by rotating the respective threaded thumb screw 216 as will be understood by one of ordinary skill in the art. The alignment of the fixture 200 relative to the bone may be checked using gunsights 208, which may include visualizing the fixture and bone using fluoroscopy as will be understood by one of ordinary skill in the art.

Once the fixture 200 is positioned, a guidance tool 100 may be inserted into the hole 206 of fixture 200. Hole 206 may be positioned along a medial or lateral side of the bone such that the guidance tool 100 is inserted into a medial or lateral aspect of the bone. The guidance tool 100 is routed through fixture 200 and along the length of the bone until a leading end extends from the inferior portion of the tibia 16 into resected joint space 22. For example, in some embodiments, the guidance tool 100 is pre-bent or has sufficient flexibility such that when the guidance tool 100 is inserted through the fixture at an angle it may be manipulated by the surgeon until the desired orientation within the bone is achieved.

With the leading end of the guidance tool 100 exposed within the resected joint space 22, a cutting tool, such as a flexible reamer, is used to prepare an intramedullary channel for receiving an implant. As described above, a flexible reamer, such as the flexible reamer described in U.S. Pat. No. 10,456,179, entitled "Intramedullary Ankle Technique and System" and which has been incorporated by reference above, is modified to provide a cannulated flexible reamer that is inserted over the leading end of guidance tool. The flexible reamer is advanced along the guidance tool 100 and up into the tibia 16 to form an intramedullary channel.

Once the intramedullary channel has been formed, the cannulated flexible reamer may be slid off of the guidance tool 100. The guidance tool 100 may then be removed from the tibia 16. Fixture 200 may then also be removed from its engagement with the bone.

In some embodiments, a guidance tool includes a body having a length extending from a first end to a second end. The body includes a shape memory section along the length of the body. The shape memory section has a curved shape.

In some embodiments, a stop is positioned along the length of the body adjacent to the first end. The stop has an enlarged dimension relative to portions of the body that are directly adjacent to the stop.

In some embodiments, the body includes a centering mechanism disposed between the stop and the first end of the body.

In some embodiments, the centering mechanism includes an expandable portion configured to expand from a collapsed configuration to an expanded configuration.

In some embodiments, the centering mechanism includes a balloon.

In some embodiments, the shape memory section is positioned between the stop and the second end of the body.

In some embodiments, the body is formed from a shape memory alloy.

In some embodiments, the shape memory alloy is selected from the group consisting of Cu—Al—Ni, NiTi, Fe—Mn—Si, Cu—Zn—Al, and Cu—Al—Ni.

In some embodiments, a method includes inserting a first end of a guidance tool into an end of a bone; advancing the guidance tool into the bone until a shape memory section of the guidance tool is disposed adjacent to the end of the bone; cutting the guidance tool at a location between the shape memory section and a second end of the guidance tool; and advancing a cutting tool along the guidance tool to form a cavity in the bone. Cutting the guidance tool allows the shape memory section of the guidance tool to regain its programmed shape.

In some embodiments, the method includes expanding a centering mechanism of the guidance tool to center the guidance tool within the bone prior to cutting the guidance tool.

In some embodiments, expanding the centering mechanism includes inflating a balloon.

In some embodiments, the cutting tool includes a cannulated flexible reamer.

In some embodiments, the cutting tool is advanced along the guidance tool until the cutting tool contacts a stop disposed adjacent to a first end of the guidance tool.

In some embodiments, the method includes resecting an end of the bone to form a resected joint space between the bone and a second bone prior to inserting the end of the guidance tool into the end of the bone.

In some embodiments, a cut end of the guidance tool extends through a window of the resected joint space when the shape memory section of the guidance tool regains its programmed shape.

In some embodiments, the bone is a tibia.

In some embodiments, a method includes coupling a fixture along a length of a bone such that a hole defined by the fixture is positioned adjacent to a side of the bone; inserting a guidance tool through the hole of the fixture and into the bone until the guidance tool extends along a length of the bone and a leading end of the guidance tool is exposed adjacent to an end of the bone; and advancing a cutting tool along the guidance tool to form a cavity in the bone.

In some embodiments, the method includes forming a resected joint space between the bone and a second bone prior to inserting the guidance tool into the bone.

In some embodiments, the bone is a tibia.

In some embodiments, the cutting tool is a cannulated flexible reamer.

In some embodiments a system includes a guidance tool and a cannulated flexible reamer. The guidance tool has a body with a length extending from a first end to a second end. The body includes a shape memory section along the length of the body. The shape memory section has a curved shape. The cannulated flexible reamer defining a channel sized and configured to receive at least a portion of the guidance tool. A leading end of the cannulated flexible reamer includes plurality of flutes.

In some embodiments, a body of the cannulated flexible reamer includes a plurality of segments. At least one of the segments is movable relative to an adjacent segment. In some embodiments, each segment is movable relative to an adjacent segment.

In some embodiments a system includes a guidance tool, a cannulated flexible reamer, and a fixture. The guidance tool has a body with a length extending from a first end to a second end. The body includes a shape memory section along the length of the body. The shape memory section has a curved shape. The cannulated flexible reamer defining a channel sized and configured to receive at least a portion of the guidance tool. A leading end of the cannulated flexible reamer includes plurality of flutes. The fixture is sized and configured to be disposed along a length of a bone. The fixture defines a hole that is positioned along the length of fixture such that, when the fixture is disposed adjacent to a bone, the guidance tool may be received in the hole of the fixture and into the bone.

In some embodiments, a body of the cannulated flexible reamer includes a plurality of segments. At least one of the segments is movable relative to an adjacent segment. In some embodiments, each segment is movable relative to an adjacent segment.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A guidance tool, comprising:
    a body having a length extending from a first end to a second end, the body including a shape memory section along the length of the body, the shape memory section having a programmed curved shape and forced to be straight by a straightening force, the straightening force removable by cutting the guidance tool;
    a stop, positioned along the length of the body adjacent to the first end, the stop having an enlarged dimension relative to portions of the body that are directly adjacent to the stop wherein the shape memory section is positioned between the stop and the second end of the body; and
    a centering mechanism disposed between the stop and the first end of the body and fixed in place relative to the body.

2. The guidance tool of claim 1, wherein the body is formed from a shape memory alloy.

3. The guidance tool of claim 2, wherein the shape memory alloy is selected from the group consisting of Cu—Al—Ni, NiTi, Fe—Mn—Si, Cu—Zn—Al, and Cu—Al—Ni.

4. A guidance tool, comprising:
    a body having a length extending from a first end to a second end, the body including a shape memory section along the length of the body, the shape memory section having a programmed curved shape and forced to be straight by a straightening force, the straightening force removable by cutting the guidance tool;
    a stop, positioned along the length of the body adjacent to the first end, having an enlarged dimension relative to portions of the body that are directly adjacent to the stop; and
    a centering mechanism disposed between the stop and the first end of the body and fixed in place relative to the body, wherein the centering mechanism includes an expandable portion configured to expand from a collapsed configuration to an expanded configuration.

5. A guidance tool, comprising:
    a body having a length extending from a first end to a second end, the body including a shape memory section along the length of the body, the shape memory section having a programmed curved shape and forced to be straight by a straightening force, the straightening force removable by cutting the guidance tool;

a stop, positioned along the length of the body adjacent to the first end, having an enlarged dimension relative to portions of the body that are directly adjacent to the stop; and a centering mechanism disposed between the stop and the first end of the body and fixed in place relative to the body, wherein the centering mechanism includes a balloon.

6. The guidance tool of claim 4 or 5, wherein the shape memory section is positioned between the stop and the second end of the body.

\* \* \* \* \*